(12) United States Patent
Jacques

(10) Patent No.: US 7,481,800 B2
(45) Date of Patent: Jan. 27, 2009

(54) TRIPLE LUMEN STONE BALLOON CATHETER AND METHOD

(75) Inventor: Steven L. Jacques, Westford, MA (US)

(73) Assignee: ConMed Endoscopic Technologies, Utica, NY (US)

(*) Notice: Subject to any disclaimer, the term of this patent is extended or adjusted under 35 U.S.C. 154(b) by 0 days.

(21) Appl. No.: 10/182,346

(22) PCT Filed: Feb. 2, 2001

(86) PCT No.: PCT/US01/03621

§ 371 (c)(1),
(2), (4) Date: Jul. 26, 2002

(87) PCT Pub. No.: WO01/56641

PCT Pub. Date: Aug. 9, 2001

(65) Prior Publication Data

US 2003/0014008 A1 Jan. 16, 2003

(51) Int. Cl.
*A61M 5/00* (2006.01)

(52) U.S. Cl. .............. 604/264; 604/96.01; 600/431

(58) Field of Classification Search ............ 604/264, 604/500, 506–510, 96.01, 102.01, 102.03, 604/103.1, 523, 528, 533–535, 284, 43–45; 606/192, 194; 600/431
See application file for complete search history.

(56) References Cited

U.S. PATENT DOCUMENTS

| | | | |
|---|---|---|---|
| 3,599,641 A * | 8/1971 | Sheridan ............ 604/256 |
| 4,641,654 A | 2/1987 | Samson et al. |
| 4,793,351 A | 12/1988 | Landman |
| 4,832,023 A * | 5/1989 | Murphy-Chutorian et al. . 606/7 |
| 4,878,495 A | 11/1989 | Grayzel |
| 4,878,898 A * | 11/1989 | Griffin et al. ............ 604/96.01 |
| 4,961,809 A | 10/1990 | Martin |
| 5,045,061 A * | 9/1991 | Seifert et al. ............ 604/96.01 |
| 5,049,132 A | 9/1991 | Shaffer et al. |
| 5,059,177 A | 10/1991 | Towne et al. |

(Continued)

FOREIGN PATENT DOCUMENTS

EP 1051990 11/2000

(Continued)

OTHER PUBLICATIONS

"Autotome™ RX Cannulating Sphincterotomes" product brochure, Boston Scientific Corporation, 2003.

(Continued)

*Primary Examiner*—Nicholas D Lucchesi
*Assistant Examiner*—Theodore J Stigell
(74) *Attorney, Agent, or Firm*—Marjama Muldoon Blasiak & Sullivan LLP

(57) ABSTRACT

A triple lumen stone balloon catheter (1) having a tapered distal end (9). A lumen (24) dedicated to transmitting contrast media is dimensioned and adapted to conform to the shape of a kidney in a main shaft of the catheter and conform to the shape of a crescent in a distal end of the catheter. The geometric shaping of the contrast media lumen (24) enables wall thickness to be maintained within acceptable ranges to sustain desirable mechanical characteristics while allowing for enhanced contrast media flow. A method for employing the balloon catheter (1) is also disclosed.

46 Claims, 13 Drawing Sheets

U.S. PATENT DOCUMENTS

| | | | |
|---|---|---|---|
| 5,078,725 A | 1/1992 | Enderle et al. | |
| 5,090,960 A | 2/1992 | Michael | |
| 5,135,599 A | 8/1992 | LeBlanc | |
| 5,156,596 A | 10/1992 | Balbierz et al. | |
| 5,327,885 A | 7/1994 | Griffith | |
| 5,378,230 A | 1/1995 | Mahurkar | |
| 5,397,302 A | 3/1995 | Weaver et al. | |
| 5,400,789 A | 3/1995 | Griffith | |
| 5,425,714 A * | 6/1995 | Johnson et al. | 604/102.02 |
| 5,437,637 A | 8/1995 | Lieber et al. | |
| 5,451,206 A | 9/1995 | Young | |
| 5,464,394 A | 11/1995 | Miller et al. | |
| 5,472,417 A | 12/1995 | Martin et al. | |
| 5,507,726 A * | 4/1996 | Johnson et al. | 604/102.02 |
| 5,512,045 A * | 4/1996 | Gurchumelidze | 604/31 |
| 5,547,469 A | 8/1996 | Rowland et al. | |
| 5,556,390 A | 9/1996 | Hicks | |
| 5,562,619 A | 10/1996 | Mirachi et al. | |
| 5,599,299 A | 2/1997 | Weaver et al. | |
| 5,643,199 A | 7/1997 | Rowland et al. | |
| 5,645,533 A | 7/1997 | Blaeser et al. | |
| 5,662,620 A | 9/1997 | Lieber et al. | |
| 5,683,362 A | 11/1997 | Rowland et al. | |
| 5,788,681 A | 8/1998 | Weaver et al. | |
| 5,824,173 A * | 10/1998 | Fontirroche et al. | 156/86 |
| 5,833,645 A | 11/1998 | Lieber et al. | |
| 5,843,028 A | 12/1998 | Weaver et al. | |
| 5,868,698 A | 2/1999 | Rowland et al. | |
| 5,876,426 A | 3/1999 | Kume et al. | |
| 5,916,193 A * | 6/1999 | Stevens et al. | 604/509 |
| 5,971,973 A | 10/1999 | Peters | |
| 6,146,354 A * | 11/2000 | Beil | 604/28 |

FOREIGN PATENT DOCUMENTS

| | | |
|---|---|---|
| WO | WO 99/07432 | 2/1999 |
| WO | WO99/17669 | 4/1999 |

OTHER PUBLICATIONS

Supplementary Search Report for European Application No. 01 905 430.3-2318, Date of Mailing Jun. 20, 2007 (5 pages total).
US 4,748,981, 06/1988, Crittenden (withdrawn)

* cited by examiner

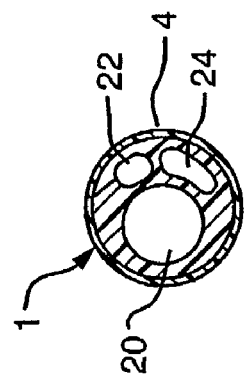
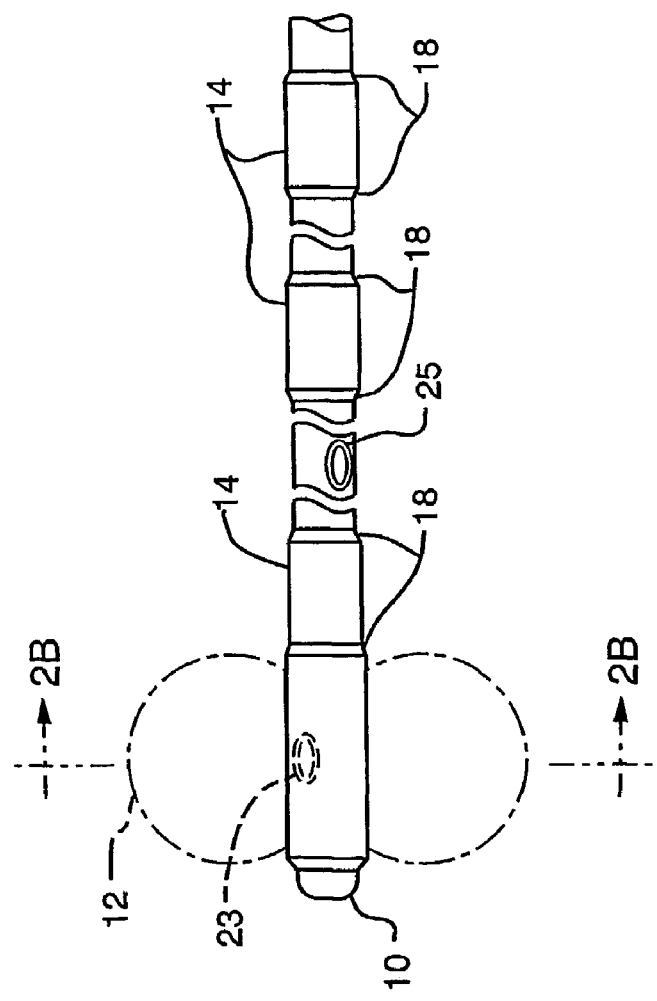

TRIPLE LUMEN STONE BALLOON CATHETER AND METHOD

FIELD OF THE INVENTION

This invention relates generally to balloon catheters having multiple lumens. Specifically, the invention relates to triple lumen stone balloon catheters and methods for making same.

BACKGROUND OF THE INVENTION

To provide an alternative to surgery, the medical industry devised non-invasive procedures and products that involve utilization of endoscopes. One such product is a stone balloon catheter. Stone balloon catheters generally comprise a sheath or elongate tube having one or multiple lumens with an elastic balloon situated proximal to a distal end of the sheath. One lumen is adapted to communicate with the interior of the balloon so that a fluid or gas source attached to a proximal end of the catheter can be used to infuse either liquid or gas into the balloon to inflate it. Any other lumen provided in the catheter can be used for a variety of purposes such as providing a channel for a guide wire to direct the insertion of the catheter into the patient.

Some of the most recent developments with stone balloon technology involves the use of a triple lumen catheter. Typically, such a catheter will have one lumen dedicated to infusion and aspiration of fluids or gases into or out of the balloon to effectuate inflation and deflation. A second lumen is dedicated to receive a guide wire for placing the catheter. A third lumen is dedicated to infuse contrast media to allow for the fluoroscopic elucidation of the site being evaluated or manipulated.

Triple lumen catheters are used for two primary purposes: 1) diagnostic and 2) therapeutic. A triple lumen stone balloon is designed particularly for use as a therapeutic tool. As the name suggests, a stone balloon is used to remove crystalline objects from a duct. One such duct is the common bile duct of the biliary system consisting of the liver, gall bladder and pancreas.

One of the enduring problems associated with catheter technology is the ability to quickly and effectively deliver contrast media to the desired locus. Due to the combination of limited lumen size and the highly viscous nature of contrast media compositions, high levels of pressure (on the order of several atmospheres), are needed to effectuate delivery of the contrast media.

It is thus, an object of the invention to provide a triple lumen stone balloon that maximizes the ease and efficiency of contrast media delivery while maintaining infusion and aspiration rates for balloon inflation and deflation and lumen size to accommodate a guide wire. It is a further object of the invention to maintain desirable mechanical characteristics of triple lumen balloon catheters while maximizing contrast media flow. These and other objects of the invention will be apparent from a reading of the following summary and detailed description of the preferred embodiment.

SUMMARY OF THE INVENTION

It has now been discovered that by balancing the relative cross-sectional areas and geometries of the lumen of a triple lumen stone balloon catheter, contrast media delivery can be maximized while maintaining acceptable inflation and deflation rates for expanding and deflating a stone balloon as well as providing adequate clearance for a guide wire. The selected geometries ensure that the following mechanical requirements are maintained. Compatibility of the guide wire lumen to receive in sliding engagement a .035 inch guide wire was maintained by using an inner diameter of about .041 inches nominal in the main shaft and about .037 inches minimum at the tip length. Balloon inflation and deflation times where maintained within acceptable ranges by reducing the cross-sectional area of the balloon inflation lumen in the main shaft and tip of the catheter.

To accommodate the high viscosity of contrast media that requires relatively high pressures to transmit the media through the main shaft of a catheter, the contrast media lumen cross-sectional area was increased and the shape of the contrast media lumen was adapted to conform to the shape of a kidney to maximize cross-sectional area while maintaining minimum wall thickness necessary to maintain the mechanical characteristics of stiffness, pushability, trackability, kinkability, tensile strength and elongation. To increase the cross-sectional area of the contrast lumen in the tip while again maintaining minimum wall thickness, the lumen was modified to conform to the shape of a crescent. Transformation from the kidney shape to the crescent shape is accomplished by adjusting the individual air pressures in each of the three lumen during sheath formation via an extrusion process.

The mechanical requirements set forth above are defined as follows. Pushability is the catheter's ability to transmit axial force to allow for transposition and placement in a particular channel or duct being negotiated. Trackability is the ability of a catheter to follow a coaxially placed guide wire. Stiffness is the relative stiffness value of the catheter relative to the stiffness of other prior art catheters. Kinkability is the ability of the main shaft and the distal tip of the catheter (approximately two inches of the shaft and tip) to sustain a 180° deflection without collapse of the lumen. Tensile strength is an axial tensile strength of greater than four pounds. Elongation is the ability of the catheter to resist stretching less than five percent when a 3.5 lb. load is attached to an end of the catheter.

To achieve these goals, a catheter was formed from Pebax 7033 medical grade having 20% Barium Sulfate. This material was chosen in part due to the fact that is meets the biological requirements of ISO 10993. The blend is easy to extrude, dimensionally stable, and provides a desired balance of mechanical characteristics such as stiffness and flexibility. The barium sulfate component provides fluoroscopic visualization capability and added stiffness to the catheter.

The main shaft of the catheter has a 7 French outside diameter that tapers down to a 5 French distal tip. The distal tip has a straight cylindrical outer shape to accommodate a balloon and marker bands as well as facilitate insertion into duct systems such as the biliary duct system. The 7 French diameter allows for the catheter to be used in a standard endoscope or duodenoscope having a 2.8 mm minimum working channel. The interluminal and exterior walls of the catheter have thickness of about 0.006 inches minimum for the main shaft and about 0.004 inches minimum for the distal tip.

BRIEF DESCRIPTION OF THE DRAWINGS

FIG. 2A is a fragmented elevational view of a distal end of a triple lumen stone balloon catheter according to one embodiment of the invention.

FIG 2B is a view and cross section of a distal end of a triple lumen stone balloon catheter according to one embodiment of the invention.

DETAILED DESCRIPTION OF THE PREFERRED EMBODIMENT

Figure 1:
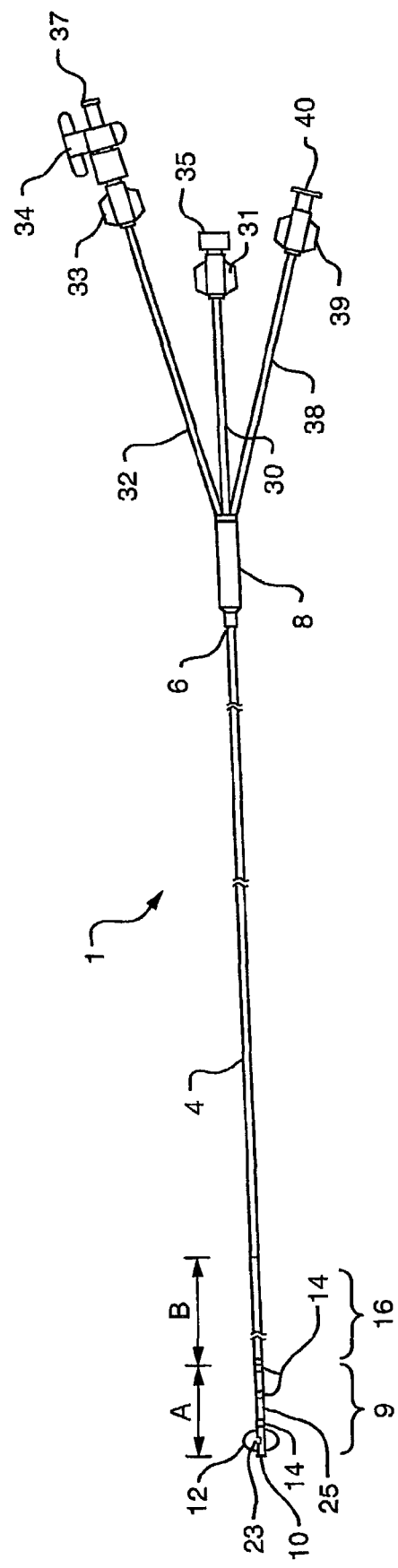
FIG. 1 is a plan view of a triple lumen balloon catheter according to one embodiment of the invention.

Referring to FIGS. 1, 2, 6-9 and 20, a triple lumen stone balloon catheter, shown generally as 1, has an elongate sheath 4 with three lumens (not shown). Sheath 4 has a proximal end 6 attached to a tube junction assembly 8 that is preferably cylindrical in shape and adapted to receive tube extension legs, described below, at a distal end of junction assembly 8. Sheath 4 has a distal end 9 that comprises a distal tip 10 that is preferably radiused to ease insertion of catheter I into a duct, particularly the common bile duct of an individual. Distal end 9 preferably conforms to the shape of a straight cylinder and is adapted to receive a stone balloon 12 that is preferably a latex based balloon. Proximal and distal ends of balloon 12 are preferably secured to distal end 9 with Loctite® adhesive.

Radio-opaque marker bands 14 (preferably less than 6 French), are provided about distal end 9 proximal to stone balloon 12 and are preferably spaced about 1 cm apart. However, marker bands 14 can be spaced any known and accepted increment to enable use as a measuring device or feature. The placement and spacing of marker bands 14 is set so that the marker bands can be used to measure the size of strictures and stones as well as to determine balloon position within a duct. Marker bands 14 are secured to distal end 9 with adhesive (not shown) and epoxy 18. An adhesive such as Loctite® is used to attach marker bands 14 to distal end 9. Epoxy 18 such as Tra-Bond epoxy is used to provide a chamfered edge to marker bands 14 as shown in FIG. 1. Distal end 9 is preferably from about 0.4" to about 2" long to accommodate the stone balloon and marker bands (shown as "A" in FIG. 1).

Extending proximally from distal end 9 is taper portion 16. Taper portion 16 is preferably from about 4" to about 20" and more preferably from about 8" to about 16" (shown as "B" in FIG. 1). A proximal end of taper 16 has an outside diameter of about 7 French while a distal end of taper 16 has an outside diameter of about 5 French.

Taper portion 16 facilitates the ease by which the catheter assembly can slide through the working channel of a duodenoscope and into the Papilla of Vater to gain entry to the common bile duct of the biliary tree.

As stated, sheath 4 has three lumens. A first lumen 20 extends from proximal end 6 to distal end 10. First lumen 20 preferably has a distal port that exists axially from distal tip 10. A portion of sheath 4 that forms a proximal end of first lumen 20 is connected to a guide wire leg extension 30. Guide wire leg extension 30 has a lumen 20a (shown in FIG. 13) that communicates with first lumen 20. Guide wire leg extension 30 has a guide wire extension leg assembly 31 that provides a finger grasp for operating leg extension 30. A luer cap 35 has threading which engages threading on a proximal end of leg extension 30. Guide wire extension leg 30 and first lumen 20 are preferably sized and adapted to receive a 0.035" guide wire. First lumen 20 and the lumen of guide wire extension leg 30 are preferably about 0.041". To provide visual reference, the phrase "0.035 guide wire" can be printed on an exterior surface of guide wire extension leg 30. Extension leg 30 can also be color-coded purple in accordance with an industry standard for a 0.035" guide wire product.

A second lumen 22 extends preferably from proximal end 6 to a point proximal to distal tip 10. Second lumen 22 has a balloon distal port 23 situated within the axial length of stone balloon 12 so that second lumen 22 communicates with an interior surface of stone balloon 12. A portion of sheath 4 that forms a proximal end of second lumen 22 is connected to a balloon extension leg 32. Balloon extension leg 32 has a lumen 22a (shown in FIG. 13) that is in communication with second lumen 22. Balloon extension leg 32 has a balloon extension leg assembly 33 that provides a finger grasp to allow ease of manipulation. Balloon extension leg assembly 33 also comprises a stopcock 34 that is preferably one-way and a luer lock section 37 to receive a balloon inflation/deflation device (not shown).

Figure 13:
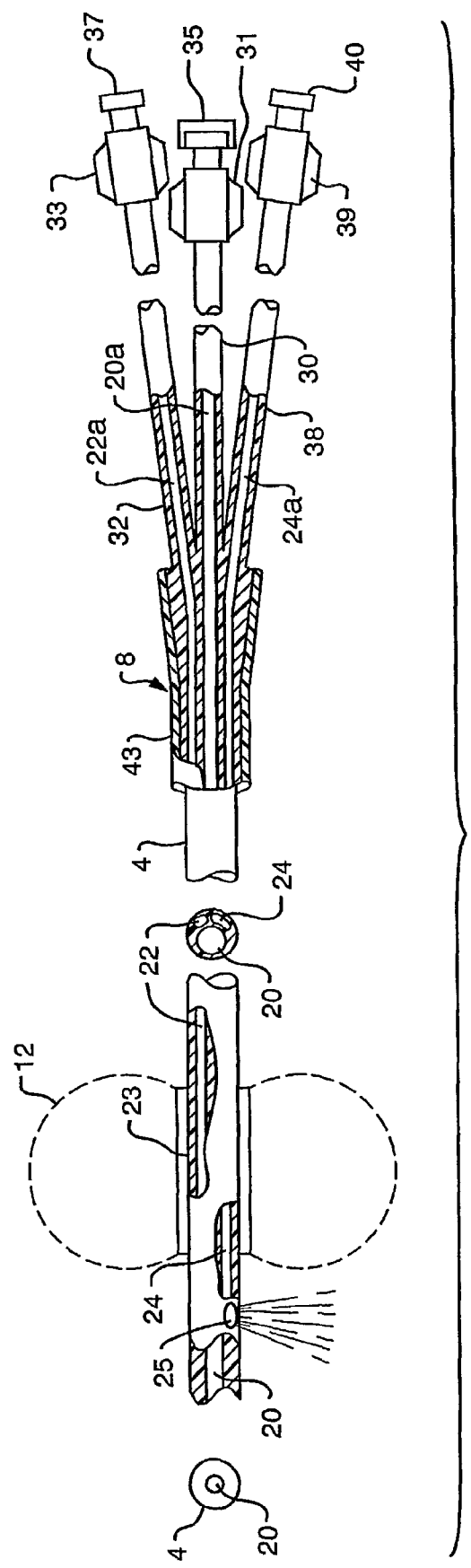
FIG. 13 is a sectional view of a triple lumen balloon catheter according to one embodiment of the invention.

A third lumen 24 extends preferably from proximal end 6 to a point proximal to stone balloon 12. Third lumen 24 has a contrast medium distal port 25 situated proximal to stone balloon 12. In an alternative embodiment (as shown in FIG. 13), distal port 25 can be situated distal to stone balloon 12. A portion of sheath 4 that forms a proximal end of third lumen 24 is connected to a contrast medium extension leg 38. Contrast medium extension leg 38 has a lumen 24a (shown in FIG. 13) that communicates with third lumen 24. Extension leg 38 has an injection leg assembly 39 that provides a finger grasp to allow ease of manipulation. Injection leg assembly 39 also has a injection luer lock 40 for receiving an injection media infusion device (not shown).

Figure 5:
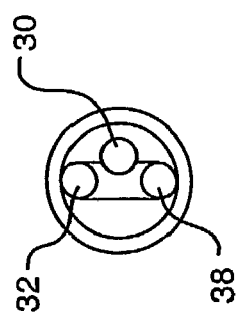
FIG. 5 is cross-sectional view of a tube junction assembly according to one embodiment of the invention.
Figure 3:
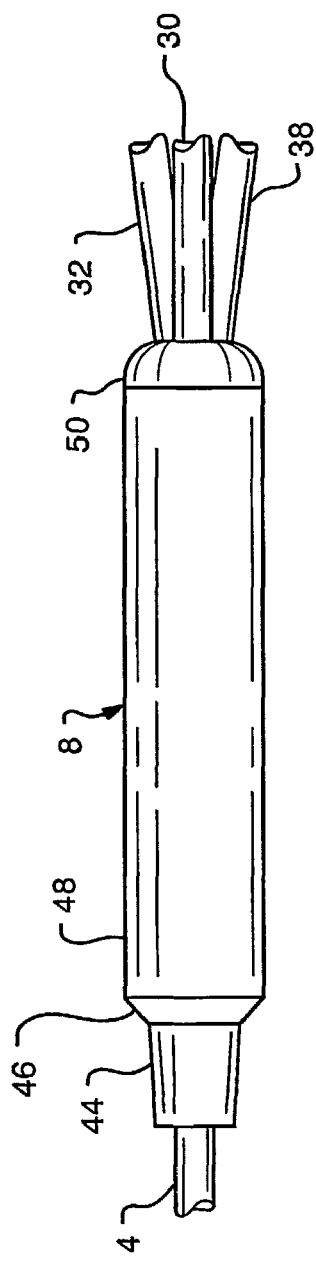
FIG. 3 is a plan view of a tube junction assembly according to one embodiment of the invention.
Figure 4:
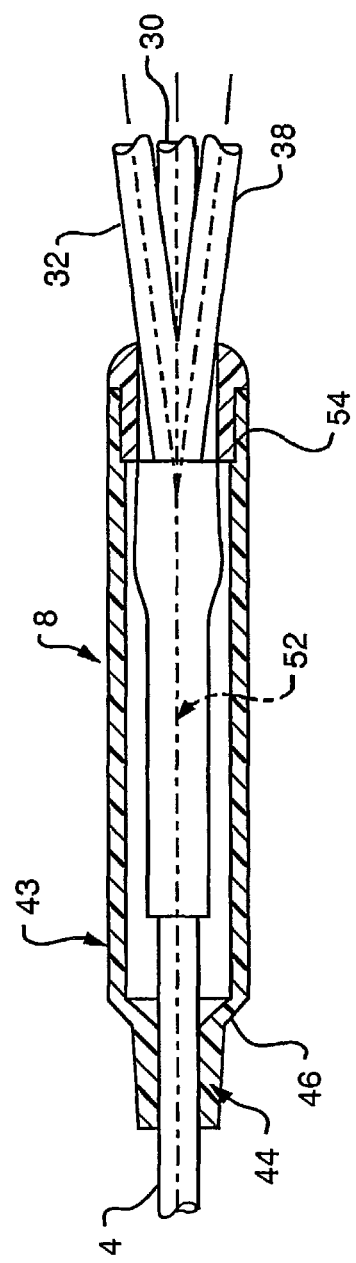
FIG. 4 is a sectional view of a tube junction assembly according to one embodiment of the invention.
Figure 6:
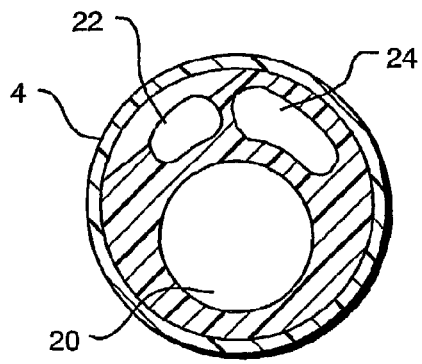
FIG. 6 is a cross-sectional view of a catheter tube according to one embodiment of the invention.
Figure 7:
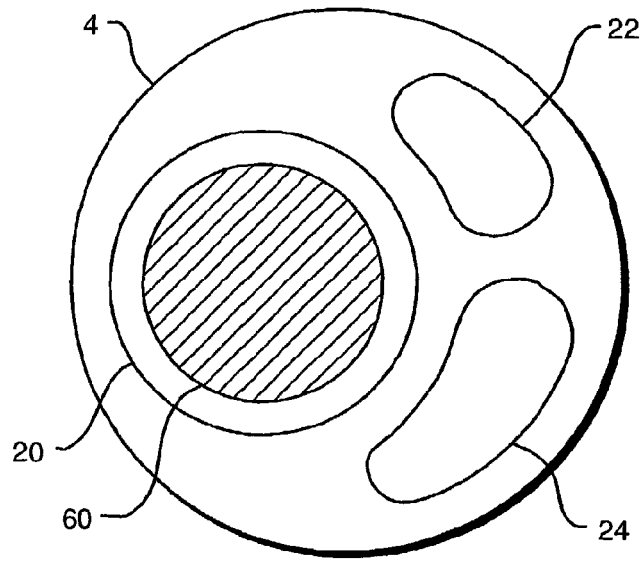
FIG. 7 is a cross-sectional view of a catheter tube distal end with guide wire according to one embodiment of the invention.
Figure 8:
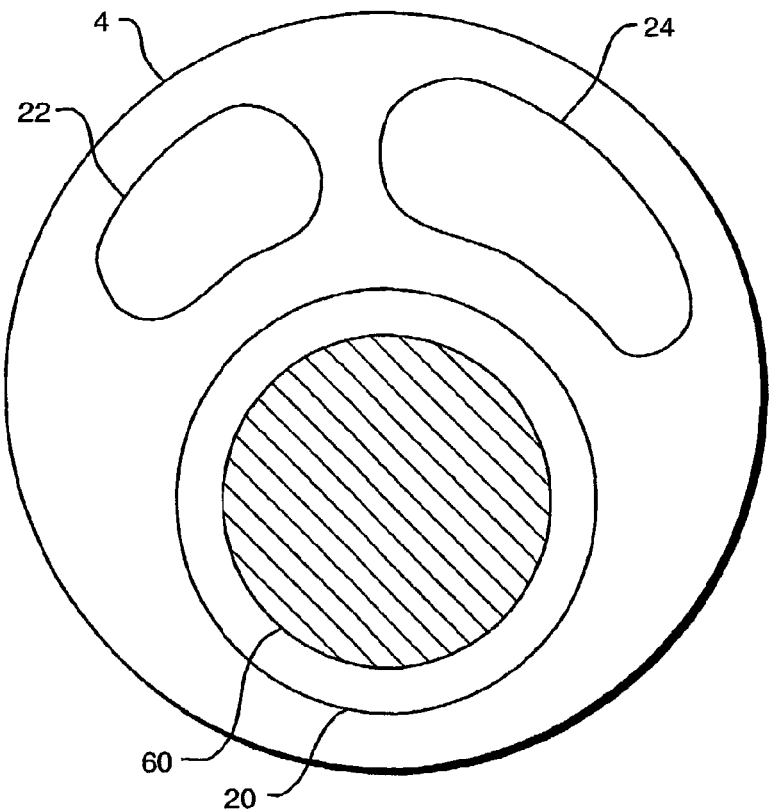
FIG. 8 is a cross-sectional view of a catheter tube main shaft with guide wire according to one embodiment of the invention.
Figure 9:
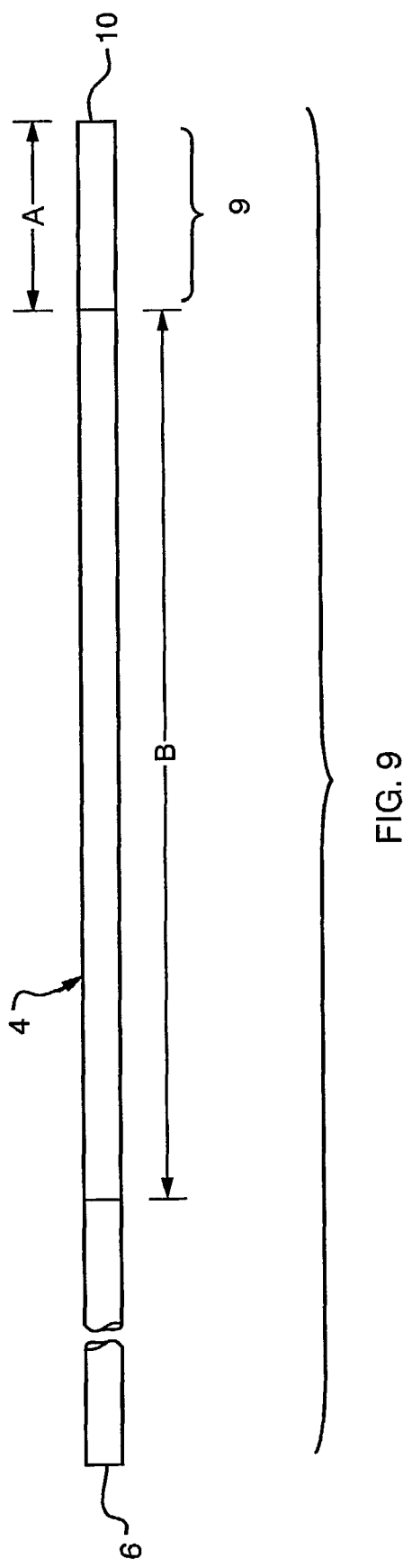
FIG. 9 is an elevational view of a catheter tube according to one embodiment of the invention.

Referring to FIGS. 3-5, tube junction assembly 8 comprises an outer trifurcate snap cover 43 adapted to secure sheath 4 to extension legs 30, 32 and 38. Snap cover 43 has a reduced diameter snap cover distal end 44 adapted to fit snugly about sheath 4. A tapered collar 46 connects snap cover distal end 44 to a main snap cover body 48. A proximal end of snap cover 43 is enclosed by a snap cap 50 that has an axial bore (not shown) to receive extension legs 30, 32 and 38. Snap cap 50 is preferably bonded to snap cover 43 with Loctite® adhesive 54. A polyolefin shrink tube 52 is provided about proximal end 6 of sheath 4 and the distal ends of extension legs 30, 32 and 38. Shrink tube 52 is heated onto the sheath and extension legs such that the materials of the components become integrated to form a seamless connection between sheath 4 and leg extensions 30, 32 and 38.

In a preferred embodiment, the wall thickness (interluminal and outside walls), of a main shaft of sheath 4 is maintained to a minimum of about 0.006". The wall thickness of distal end 9 is maintained to a minimum of about 0.004". These values are essential to maintain acceptable mechanical characteristics of pushability, trackability, stiffness, kinkability, tensile strength and elongation. I have discovered that these wall thickness can be maintained while maximizing the cross-sectional area of third lumen 38, the contrast media lumen, that provides enhanced contrast media flow through catheter 1. To optimize the flow of contrast media, the diameter of first lumen 20 was reduced to about 0.041" in the main shaft and 0.037" minimum in the tip length that is sufficient to allow for the free movement of a guide wire 60 through first lumen 20.

Figure 12:
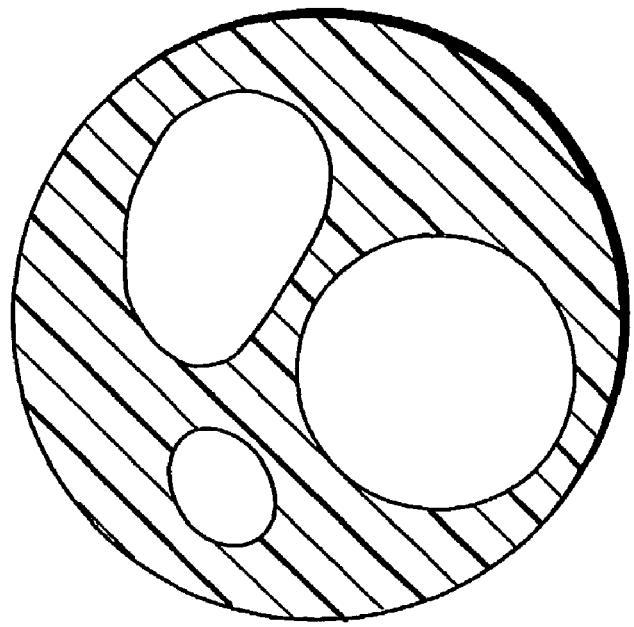
FIG. 12 is a cross-sectional view of a main shaft end of a catheter tube according to one embodiment of the invention.
Figure 11:
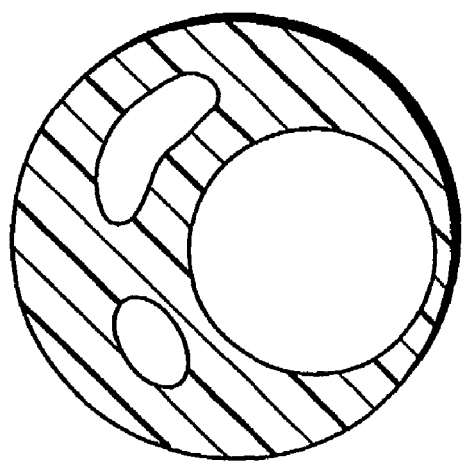
FIG. 11 is a cross-sectional view of a distal end of a catheter tube according to one embodiment of the invention.

Second lumen 22, the balloon inflation/deflation lumen, was also reduced in diameter without any appreciable effect on the inflation or deflation rates. This downsizing provided more space to enlarge third lumen 38, the contrast media lumen. To ensure desired flow, the diameter of the proximal end of second lumen 22 is maintained to allow for the insertion of a 0.014 inch diameter pin. The cross-sectional shape of second lumen 22 does not have to be maintained circular but may take on other irregular or regular shapes such as an oval I discovered that a cross-sectional shape that conforms to a kidney shape for third lumen 38 in the main shaft (the portion of sheath 4 that does not include the tapered distal end), of sheath 4 maximized the flow rate of contrast medium in the third lumen. The kidney shaped lumen is shown in FIG. 12. I also discovered that a cross-sectional shape that conforms to a crescent shape for third lumen 38 in distal end 9 of sheath 4 maximized contrast media flow rates in that portion of sheath 4 while maintaining the set minimum wall thickness. The crescent shaped lumen is shown in FIG. 11.

Figure 14A:
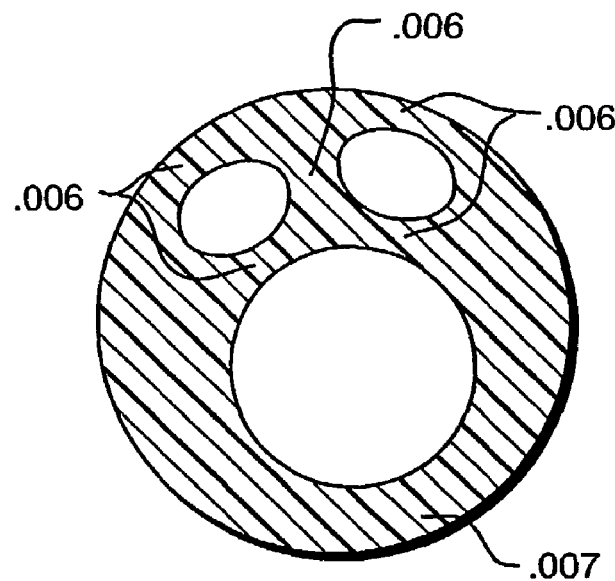
FIGS. 14A and 14B are cross-sectional views of a prior art balloon catheter designated "A".
Figure 14B:
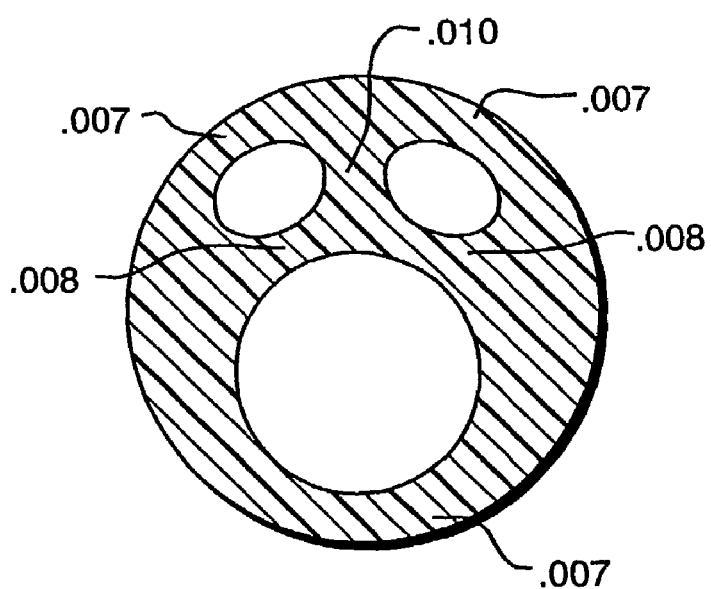
Figure 15A:
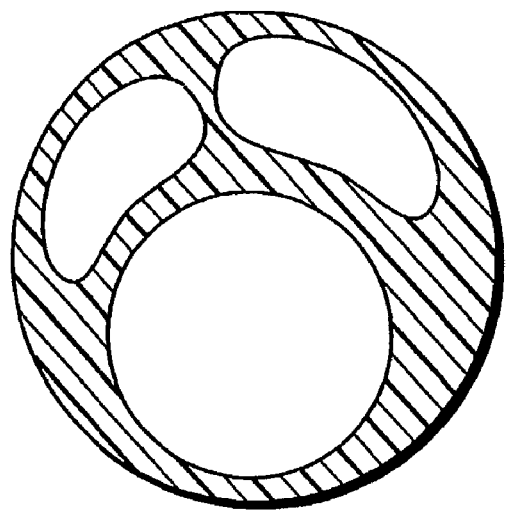
FIGS. 15A and 15B are cross-sectional views of a prior art balloon catheter designated "B".
Figure 15B:
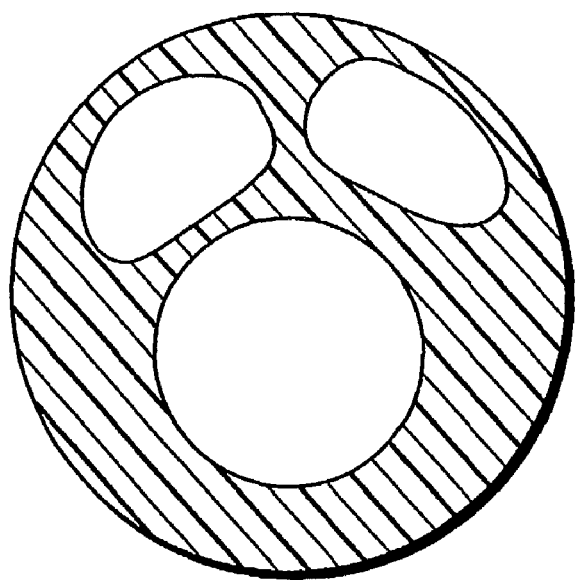

To demonstrate the efficacy of the invention, a comparison test was run with prior art products. Prior art triple lumen catheter A is shown in FIGS. 14A and 14B. Prior art triple lumen catheter B is shown in FIGS. 15A and 15B. The invention catheter is shown in FIGS. 11 and 12. All three have 7 French main body outer diameters that reduce down to 5 French distal tip outer diameters. Each has an 11.5 mm balloon attached proximal to the distal ends of the catheters. As is clearly seen in the figures, the invention catheter has the smallest cross-sectional area for the balloon inflation lumen and the largest cross-sectional area for the contrast media lumen.

To test balloon inflation/deflation rates, 1.5 cc of air was infused into the 11.5 mm balloons with a preloaded syringe. Three test runs were made with the prior art balloon catheters and over thirty runs were made with the invention balloon catheter. Prior art catheter A had a mean inflation rate of 1.18 seconds with a standard deviation of 0.13. Prior art catheter B had a mean inflation rate of 0.92 seconds with a standard deviation of 0.13. The invention catheter had a mean inflation rate of 0.74 seconds with a standard deviation of 0.08.

Prior art catheter A had a mean deflation rate of 1.00 seconds with a standard deviation of 0.03. Prior art catheter B had a mean deflation rate of 0.94 seconds with a standard deviation of 0.14. The invention catheter had a mean deflation rate of 0.57 seconds with a standard deviation of 0.08.

To test contrast lumen injection rates, tests were conducted with water being infused through the contrast lumen at 60 psi. The rate was determined by dividing the amount of water collected at the distal ends of the catheters by the time. Tests were run for versions of balloon catheters having contrast lumen distal ports proximal to the balloon and versions having distal ports distal to the balloon.

For versions having contrast lumen distal to the balloon, prior art catheter A had a mean flow rate of 21.7 ml/min. with a mean deviation of 0.6. Prior art catheter B had a mean flow rate of 43.7 ml/min. with a mean deviation of 0.6. The invention catheter had a mean flow rate of 48 ml/min. with a mean deviation of 2.

For the catheter versions having contrast lumen proximal to the balloon, prior art catheter A had a mean flow rate of 23.0 ml/min. with a mean deviation of 1.7. Prior art catheter B had a mean flow rate of 44.3 ml/min. with a mean deviation of 1.5. The invention catheter had a mean flow rate of 52 ml/min. with a mean deviation of 2.

The chart set forth below lists the preferred maximum and minimum cross-sectional areas for the invention triple lumen balloon catheter. It is to be understood that these values are extremes for catheters made with Pebax 7033. Use of other materials may allow for larger maximums and smaller minimums while achieving and maintaining the flow rates and mechanical characteristics set forth herein. Other materials may also be used to alter the mechanical characteristics, e.g., trackability and kinkability, without altering the desired lumen cross-sectional areas and improved flow rates and without departing from the scope of the invention.

Figure 16:
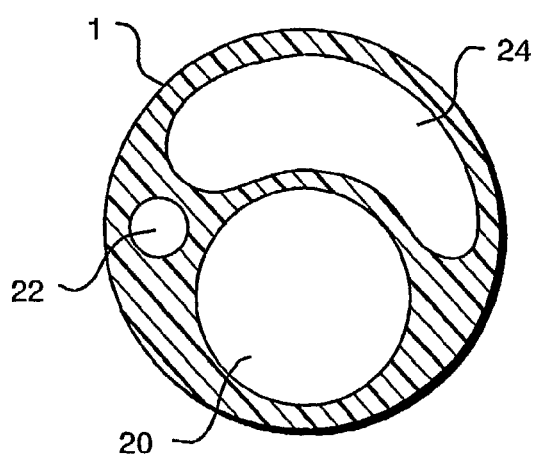
FIG. 16 is a cross-sectional view of a catheter with a preferred maximum contrast medium lumen in the distal tip according to one embodiment of the invention.
Figure 17:
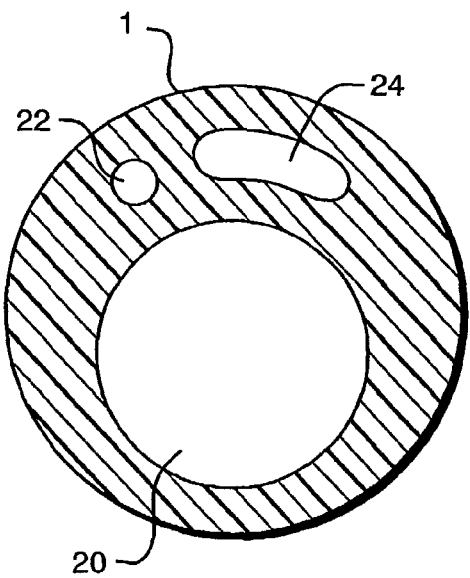
FIG. 17 is a cross-sectional view of a catheter with a preferred minimum contrast medium lumen in the distal tip according to another embodiment of the invention.
Figure 18:
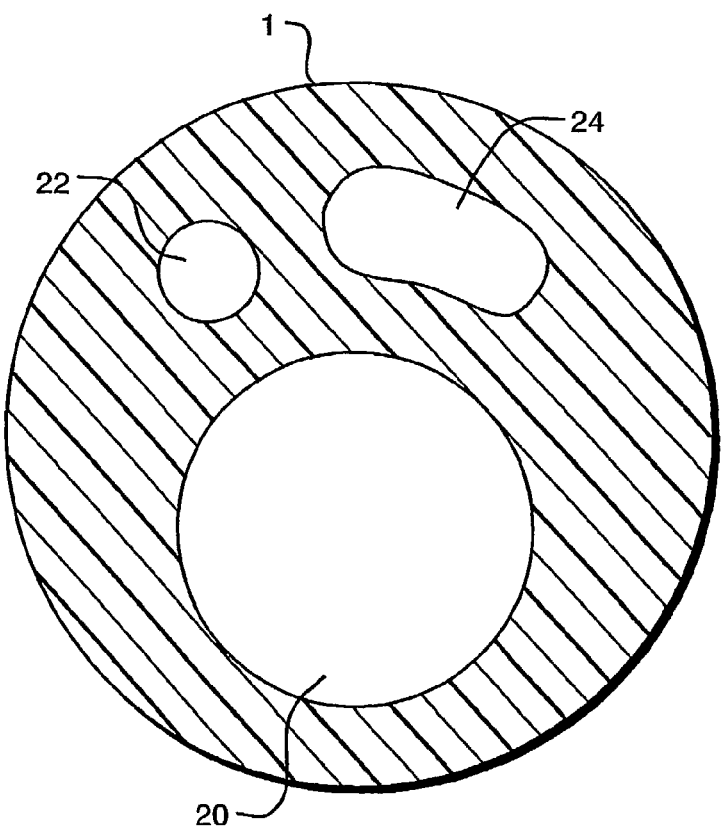
FIG. 18 is a cross-sectional view of a catheter with a preferred minimum contrast medium lumen in the main shaft according to one embodiment of the invention
Figure 19:
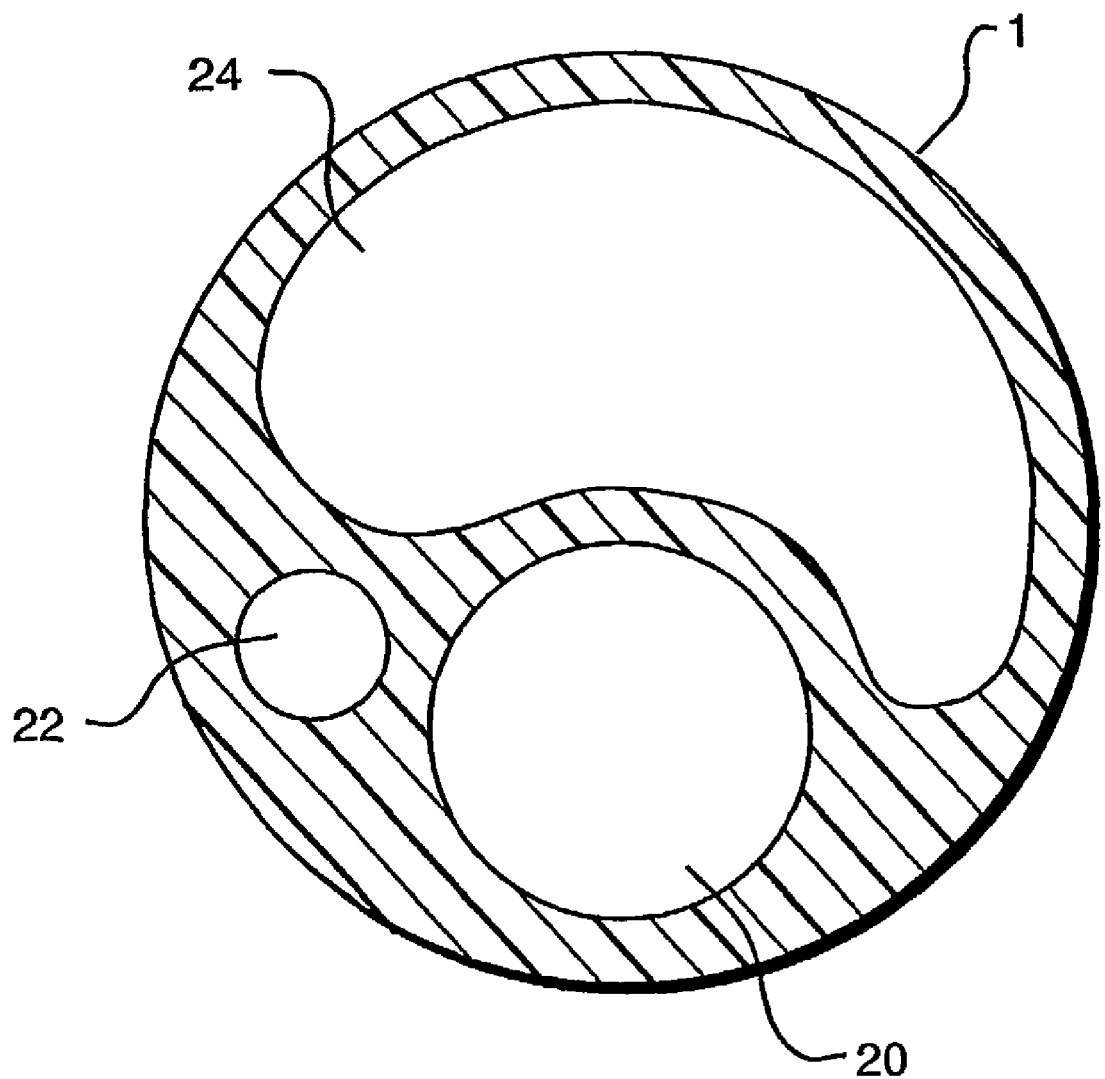
FIG. 19 is a cross-sectional view of a catheter with a preferred maximum contrast medium lumen in the main shaft according to another embodiment of the invention.
Figure 20:
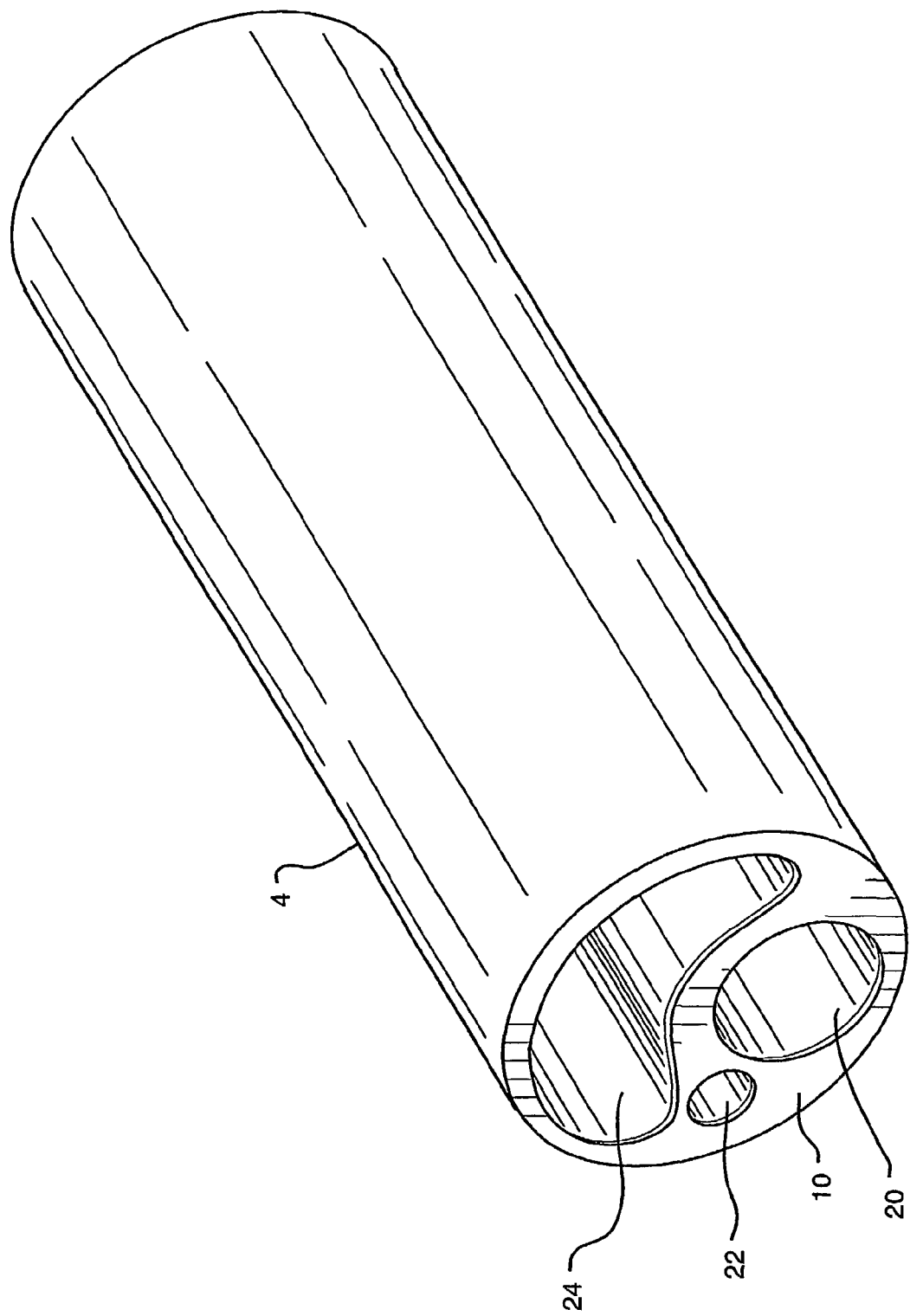
FIG. 20 is a perspective view of a triple lumen catheter according to one embodiment of the invention.

FIG. 16 shows a cross-section of a distal tip of a catheter made in accordance with one embodiment of the invention with the contrast media lumen maximized relative to the balloon lumen and the guide wire lumen. FIG. 17 shows a cross-section of a distal tip of a catheter made in accordance with another embodiment of the invention with the contrast media lumen minimized relative to the balloon lumen and the guide wire lumen. FIG. 18 shows a cross-section of a main shaft of a catheter made in accordance with one embodiment of the invention with the contrast media lumen minimized relative to the balloon lumen and the guide wire lumen. FIG. 19 shows a cross-section of a main shaft of a catheter made in accordance with another embodiment of the invention with the contrast media lumen maximized relative to the balloon lumen and the guide wire lumen. The cross-sectional areas of the lumens shown in the drawings are reflected in the chart below.

| Catheter Location | Guide wire Lumen (in$^2$) | | Balloon Lumen (in$^2$) | | Contrast Lumen (in$^2$) | |
| --- | --- | --- | --- | --- | --- | --- |
| | Min. | Max. | Min. | Max. | Min. | Max. |
| Tip Length | $1.08 \times 10^{-3}$ | $1.20 \times 10^{-3}$ | $2.83 \times 10^{-5}$ | $9.14 \times 10^{-5}$ | $1.42 \times 10^{-4}$ | $1.07 \times 10^{-3}$ |
| Main Shaft | $1.19 \times 10^{-3}$ | $1.59 \times 10^{-3}$ | $1.13 \times 10^{-4}$ | $2.07 \times 10^{-4}$ | $3.48 \times 10^{-4}$ | $3.15 \times 10^{-3}$ |

The desired lumen geometric configurations are established by varying the pressures in the different lumen when sheath 4 is manufactured using an extrusion process. Altering the pressure differentials in the lumens during the extrusion process produces varied geometric cross-sections. One set of pressure differentials is used in the main shaft while a different set is used in the distal end. This was combined with what is commonly known in the industry as the "bump" tubing extrusion process to generate a tapered distal end with cylindrical tip. The tapered distal end is formed by increasing the extrusion speed at the appropriate point in the formation of sheath 4.

Those of skill in the art will appreciate that the process is a dynamic one that cannot be operated at a constant set point throughout the process. Multipoint output speed controls allow for the smooth transition of the outside geometry of the sheath that is preferably circular in cross section. Multipoint pressure controls are essential to obtain the desired cross sectional areas and geometries of the three lumens.

To illustrate the process, to make the crescent shaped contrast media lumen in the distal end, the pressure in the guide wire lumen is slightly decreased from the pressure used in the main shaft which is approximately from about 3 to 8 inches of $H_2O$ and preferably from about 4 to about 6 inches of $H_2O$ to achieve a drop in inner diameter of from 0.041 inches to 0.037 inches. The pressure in the balloon inflation lumen was reduced to close to zero without any adverse results to the dimensional integrity of the balloon inflation lumen in the distal end. The pressure in the contrast medium lumen was slightly increased within the range of approximately from about 3 to about 8 inches of $H_2O$ and preferably from about 4 to about 6 inches of $H_2O$. The shift in relative lumen pressures resulted in the contrast medium lumen migrating into the areas previously occupied by the balloon lumen.

Those of ordinary skill in the art will be familiar with the chemical compositions, materials and methods used to make such catheters. It is to be understood that the composition of sheath 4 does not form part of the invention. The materials described herein are merely for illustrative purposes.

It is to be appreciated that due to variances from batch to batch of a selected material and variances among different materials, some experimentation is required with respect to the pressure and speed settings to achieve the desired geometric configurations described herein. The pressure ranges set forth herein are for the disclosed Pebax material. Alternative ranges may be required for different materials to achieve the desired geometric configurations. The key to formation of the desired geometric configurations lies with the balance of pressure differentials in the various lumen at any given point along the extrusion process as well as pressure alteration in the individual lumen as the extrusion progresses.

Figure 10:
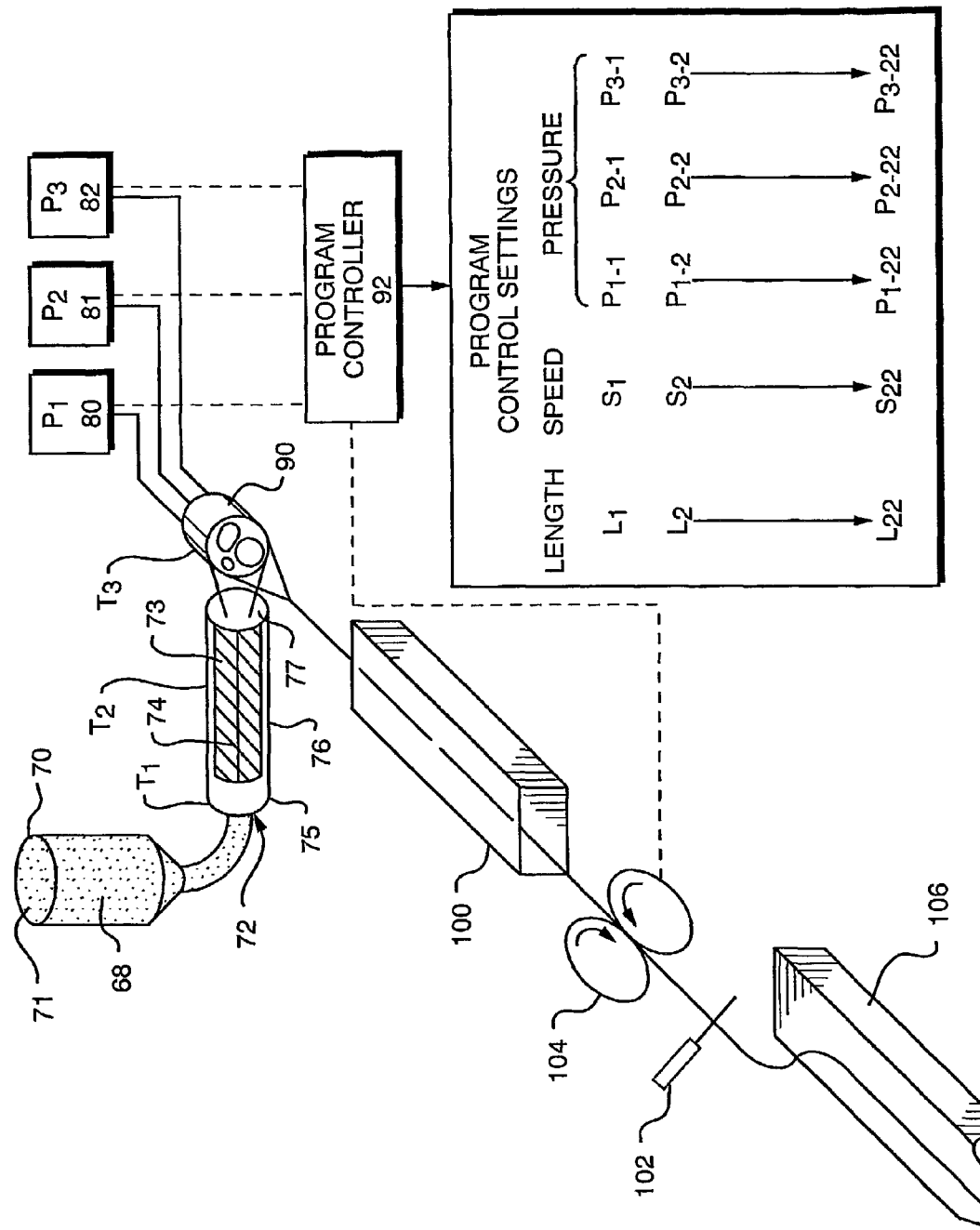
FIG. 10 is a schematic of a catheter tube manufacturing apparatus and process according to one embodiment of the invention.

The apparatus shown in FIG. 10 is used to make sheath 4. The process begins by placing resin 68 in a resin dryer 70 that has a hollow chamber 71 for receiving resin 68. Resin 68 is maintained in dryer 70 overnight to remove any moisture present in the resin. Dryer 70 is attached to a heating chamber 72 having a hollow portion 73 for receiving a screw feed 74. Screw feed 74 rotates within heating chamber 72. Hollow portion 73 is in communication with hollow chamber 71. Screw feed 74 has a proximal end 75, the pre-screw feed end, that is set at a first temperature, a middle screw feed section 76, the mid-screw section, that is set at a second temperature and a distal screw feed end 77, the extrusion die end, that is set at a third temperature. The temperatures are set according to resin melt characteristics as is well known in the art.

To form the three lumen, three high speed, ultra low pressure air controllers, first air controller 80, second air controller 81 and third air controller 82 are attached to a three lumen extrusion die 90 and a program controller 92. Custom software is loaded into program controller 92 and controls five outputs-processing speed, the pressure in the three lumens and the length of the finished product. The Program controller has twenty-two adjustment points for the five output settings.

The heated resin 68 is fed through extrusion die 90. The formed catheter is then placed in a water bath 100 to cool the extruded catheter sheath. The sheath is then fed by rollers 104 past a computer operated cut-off blade 102 that cuts the tube into predetermined lengths. The severed catheter lengths are dropped into a tray 106 where the catheters can be gathered for further assembly.

To initiate the process, an extrusion run is commenced and dimensional samples are taken to determine whether the desired dimensional parameters are being met. Adjustments are made to the apparatus until the desired dimensions are obtained. The extrusion run is dimensionally monitored throughout the run. Data is submitted with each lot to ensure consistency and acceptability of the product.

The inventive catheter described herein may be used in the following manner to evaluate, for example, a bile duct site and to position a balloon for treating a stricture or obstruction. An endoscope such as a duodenoscope is advanced through the alimentary track to the Papilla of Vater. A 0.035 inch guide wire is advanced through the working channel of the endoscope, out the endoscope's distal end and advanced through the Papilla of Vater into the common bile duct. A proximal end of the guide wire is inserted into a distal port of the guide wire lumen of catheter 1. Catheter 1 is advanced along the guide wire and through the endoscope working channel until positioned in the common bile duct or other desired duct. Alternatively, the guide wire can be preloaded into the catheter and the combination of the catheter and guide wire can be advanced through the endoscope to the desired duct site. Contrast media can then be infused through the novel contrast media lumen to enable visualization of the duct anatomy and contents and to adjust the catheter's positioning with respect to any potential duct occlusions or stones. Once positioning of the balloon has been finalized via the radiopaque markers, the contrast media or a combination of both, inflation media is infused through the balloon inflation/deflation lumen to expand the balloon. The catheter is then manipulated to remove the obstruction or stricture.

The techniques used to operate the catheter are those that are common in the art. The primary difference is the ease with which contrast media can be infused into a desired site due to the unique combination of lumen geometries and cross-sectional areas.

It is to be understood that the foregoing description of the invention is intended merely to be illustrative thereof and that other modifications, embodiments and equivalents may be apparent to those who are skilled in the art without departing from its spirit.

The invention claimed is:

1. A multi-lumen balloon catheter comprising:
a sheath comprising a main body and a distal end extending distally from the main body and a plurality of lumens comprising a first lumen, second lumen, and third lumen;
the third lumen formed in the sheath wherein a first portion of the third lumen extends at least partially through the main body and has a first shape in cross section and wherein a second portion of the third lumen extends at least partially through the distal end and has a second, different shape in cross section;
the second lumen extending at least partially through the main body and partially through the distal end;
the first lumen extending at least partially through the main body and partially through the distal end;
a balloon attached about the distal end; and
a taper portion extending proximally from the distal end, wherein the outside diameter of the sheath at the distal end is smaller than the outside diameter of the sheath at the proximal end of the taper portion, the plurality of lumens extending through the taper portion.

2. The catheter of claim 1 wherein the cross-sectional area of the first portion of the third lumen is from about $3.48 \times 10^{-4}$ inches$^2$ to about $3.15 \times 10^{-3}$ inches$^2$.

3. The catheter of claim 1 wherein the cross-sectional area of the second portion of the third lumen is from about $1.42 \times 10^{-4}$ inches$^2$ to about $1.07 \times 10^{-3}$ inches$^2$.

4. The catheter of claim 1 wherein the second lumen has a first portion that extends at least partially through the main body and a second portion that extends at least partially through the distal end.

5. The catheter of claim 4 wherein the first portion of the second lumen has a cross-sectional area from about $1.13 \times 10^{-4}$ inches$^2$ to about $2.07 \times 10^{-4}$ inches$^2$.

6. The catheter of claim 4 wherein the second portion of the second lumen has a cross-sectional area from about $2.83 \times 10^{-5}$ inches$^2$ to about $9.14 \times 10^{-5}$ inches$^2$.

7. The catheter of claim 1 wherein the first lumen has a first portion that extends at least partially through the main body and a second portion that extends at least partially through the distal end.

8. The catheter of claim 7 wherein the first portion of the first lumen has a cross-sectional area from about $1.19 \times 10^{-3}$ inches$^2$ to about $1.59 \times 10^{-3}$ inches$^2$.

9. The catheter of claim 7 wherein the second portion of the first lumen has a cross-sectional area from about $1.08 \times 10^{-3}$ inches$^2$ to about $1.20 \times 10^{-3}$ inches$^2$.

10. The catheter of claim 1 wherein the main body has an external wall and interluminal walls wherein the external and interluminal walls have a minimum thickness of about .006 inches.

11. The catheter of claim 1 wherein the distal end has an external wall and interluminal walls wherein the external and interluminal walls have a minimum thickness of about .004 inches.

12. The catheter of claim 1 wherein the first shape is a kidney shape and the second shape is a crescent shape.

13. A multi-lumen balloon catheter comprising:
a sheath comprising a main body and a distal end extending distally from the main body and a plurality of lumens comprising a first lumen, second lumen, and third lumen;
third lumen formed in the sheath wherein a first portion of the third lumen extends at least partially through the main body and has a first shape in cross section and a cross-sectional area from about $3.48 \times 10^{-4}$ inches$^2$ to about $3.15 \times 10^{-3}$ inches$^2$ and, wherein a second portion of the third lumen extends at least partially through the distal end and has a second, different shape in cross section and has a cross-sectional area from about $1.42 \times 10^{-4}$ inches$^2$ to about $1.07 \times 10^{-3}$ inches$^2$;
the second lumen extending at least partially through the main body and partially through the distal end;
the first lumen extending at least partially through the main body and partially through the distal end;
a balloon attached about the distal end; and
a taper portion extending proximally from the distal end, wherein the outside diameter of the sheath at the distal end is smaller than the outside diameter of the sheath at the proximal end of the taper portion, the plurality of lumens extending through the taper portion.

14. The catheter of claim 13 wherein the second lumen has a first portion that extends at least partially through the main body and a second portion that extends at least partially through the distal end wherein the cross-sectional area of the first portion of the second lumen is from about $1.13 \times 10^{-4}$ inches to about $2.07 \times 10^{-4}$ inches and the cross-sectional area of the second portion of the second lumen is from about $2.83 \times 10^{-5}$ inches$^2$ to about $9.14 \times 10^{-5}$ inches$^2$.

15. The catheter of claim 13 or 14 wherein the first lumen has a first portion that extends at least partially through the main body and a second portion that extends at least partially through the distal end wherein the cross-sectional area of the first portion of the first lumen is from about $1.19 \times 10^{-3}$ inches to about $1.59 \times 10^{-3}$ inches$^2$ and the cross-sectional area of the second portion of the first lumen is from about $1.08 \times 10^{-3}$ inches$^2$ to about $1.20 \times 10^{-3}$ inches$^2$.

16. The catheter of claim 15 wherein the main body has an outside wall and interluminal walls and wherein the minimum wall thickness of the outside and interluminal main body walls is about .006 inches.

17. The catheter of claim 13 or 14 wherein the main body has an outside wall and interluminal walls and wherein the minimum wall thickness of the outside and interluminal main body walls is about .006 inches.

18. The catheter of claim 17 wherein the distal end has an outside wall and interluminal walls and wherein the minimum wall thickness of the outside and interluminal distal end walls is about .004 inches.

19. The catheter of claim 18 wherein the main body has an outside diameter of about 7 French and the distal end has an outside diameter of about 5 French.

20. The catheter of claim 13 wherein the first shape is a kidney shape and the second shape is a crescent shape.

21. A sheath comprising:
a main body and a distal end extending distally from the main body and a plurality of lumens comprising a contrast media lumen, a second lumen, and a third lumen;

the contrast media lumen formed in the sheath wherein a first portion of the contrast media lumen extends at least partially through the main body and has a first shape in cross section and wherein a second portion of the contrast media lumen extends at least partially through the distal end and has a second, different shape in cross section;

the second lumen extending at least partially through the main body and partially through the distal end;

the third lumen extending at least partially through the main body and partially through the distal end; and a taper portion extending proximally from the distal end, wherein the outside diameter of the sheath at the distal end is smaller than the outside diameter of the sheath at the proximal end of the taper portion, the plurality of lumens extending through the taper portion.

22. The sheath of claim 21 wherein the second lumen has a first portion that extends at least partially through the main body and has a diameter of about .041 inches and a second portion that extends at least partially through the distal end and has a diameter of about .037 inches.

23. The sheath of claim 21 or 22 further comprising a balloon attached about the distal end.

24. The sheath of claim 21 wherein the first shape is a kidney shape and the second shape is a crescent shape.

25. An endoscopic method of evaluating and treating an occluded duct comprising the steps of providing a catheter having at least three lumens comprising:
  a sheath having a main body and a distal end extending distally from the main body,
  a balloon attached about the distal end, wherein the balloon has an inner surface,
  a third lumen for contrast media, wherein the third lumen has a first portion having a kidney shape in cross section and extending at least partially through the main body and a second portion having a crescent shape in cross section and extending at least partially through the distal end;
  a second lumen extending at least partially through the main body and partially through the distal end and having a distal port in communication with the inner surface of the balloon and a proximal port to receive inflation media;
  a first lumen extending at least partially through the main body and at least partially through the distal end wherein the first lumen has a distal port in the distal end and is adapted to receive a guide wire;
  providing an endoscope having a working channel;
  advancing the endoscope into proximity with a duct system;
  advancing a guide wire through the working channel of the endoscope, out the endoscope's distal end, and into a desired position in the duct system;
  placing the guide wire into the distal port of the first lumen and sliding the catheter over the guide wire and through the endoscope;
  positioning the catheter in the duct system;
  infusing contrast media through the third lumen; and
  infusing inflation media into the second lumen to expand the balloon.

26. An endoscopic method of evaluating and treating an occluded duct, comprising the steps of providing a catheter having at least three lumens comprising:
  a sheath having a main body and a distal end extending distally from the main body,
  a balloon attached about the distal end, wherein the balloon has an inner surface,
  a third lumen for contrast media, wherein the third lumen has a first portion having a kidney shape in cross section and extending at least partially through the main body and a second portion having a crescent shape in cross section and extending at least partially through the distal end;
  a second lumen extending at least partially through the main body and partially through the distal end and having a distal port in communication with the inner surface of the balloon and a proximal port to receive inflation media;
  a first lumen extending at least partially through the main body and at least partially through the distal end wherein the first lumen has a distal port in the distal end and is adapted to receive a guide wire;
  providing an endoscope having a working channel;
  advancing the endoscope into proximity with a duct system;
  preloading the guide wire into the first lumen of the catheter and advancing the guide wire and the catheter together through the working channel of the endoscope, out the endoscope's distal end, and into a desired position in the duct system;
  infusing contrast media through the third lumen; and
  infusing inflation media into the second lumen to expand the balloon.

27. The method of claim 25 or 26 wherein the first portion of the third lumen has a cross-sectional area of from about $3.48 \times 10^{-4}$ inches$^2$ to about $3.15 \times 10^{-3}$ inches$^2$ and, wherein a second portion of the third lumen has a cross-sectional area from about $1.42 \times 10^{-4}$ inches$^2$ to about $1.07 \times 10^{-3}$ inches$^2$.

28. The method of claim 27 wherein the first portion of the second lumen has a cross-sectional area from about $1.13 \times 10^{-4}$ inches$^2$ to about $2.07 \times 10^{-4}$ inches$^2$ and the second portion of the second lumen has a cross-sectional area from about $2.83 \times 10^{-5}$ inches$^2$ to about $9.14 \times 10^{-5}$ inches$^2$.

29. The method of claim 25 wherein the first portion of the first lumen has a cross-sectional area from about $1.19 \times 10^{-3}$ inches$^2$ to about $1.59 \times 10^{-3}$ inches$^2$ and the second section of the first lumen has a cross-sectional area from about $1.08 \times 10^{-3}$ inches$^2$ to about $1.20 \times 10^{-3}$ inches 30. The method of claim 27 wherein the main body has an outside wall and interluminal walls and wherein the minimum wall thickness of the outside and interluminal main body walls is about .006 inches.

31. The method of claim 30 wherein the distal end has an outside wall and interluminal walls and wherein the minimum wall thickness of the outside and interluminal distal end walls is about .004 inches.

32. The method of claim 31 wherein the main body has an outside diameter of about 7 French and the distal end has an outside diameter of about 5 French.

33. A multi-lumen balloon catheter comprising:
  a sheath comprising a main body and a distal end extending distally from the main body and a plurality of lumens comprising a first lumen, second lumen, and third lumen;
  the third lumen formed in the sheath wherein a first portion of the third lumen extends at least partially through the main body and has a first shape in cross section and wherein a second portion of the third lumen extends at least partially through the distal end and has a second, different shape in cross section;
  the second lumen extending at least partially through the main body and partially through the distal end;
  the first lumen extending at least partially through the main body and partially through the distal end;

a balloon attached about the distal end;

wherein the third lumen transitions from the first shape to the second shape at a point, or over a region, that is proxmal to the balloon; and a taper portion extending proximally from the distal end, wherein the outside diameter of the shealth at the distal end is smaller than the outside diameter of the shealth at the proximal end of the taper portion, the plurality of lumens extending through the taper portion.

34. The catheter of claim 33 wherein the cross-sectional area of the first portion of the third lumen is from about $3.48 \times 10^{-4}$ inches$^2$ to about $3.15 \times 10^{-3}$ inches$^2$.

35. The catheter of claim 33 wherein the cross-sectional area of the second portion of the third lumen is from about $1.42 \times 10^{-4}$ inches$^2$ to about $1.07 \times 10^{-3}$ inches$^2$.

36. The catheter of claim 33 wherein the second lumen has a first portion that extends at least partially through the main body and a second portion that extends at least partially through the distal end.

37. The catheter of claim 36 wherein the first portion of the second lumen has a cross-sectional area from about $1.13 \times 10^{-4}$ inches$^2$ to about $2.07 \times 10^{-4}$ inches$^2$.

38. The catheter of claim 36 wherein the second portion of the second lumen has a cross-sectional area from about $2.83 \times 10^{-5}$ inches to about $9.14 \times 10^{-5}$ inches$^2$.

39. The catheter of claim 33 wherein the first lumen has a first portion that extends at least partially through the main body and a second portion that extends at least partially through the distal end.

40. The catheter of claim 39 wherein the first portion of the first lumen has a cross-sectional area from about $1.19 \times 10^{-3}$ inches$^2$ to about $1.59 \times 10^{-3}$ inches$^2$.

41. The catheter of claim 39 wherein the second portion of the first lumen has a cross-sectional area from about $1.08 \times 10^{-3}$ inches$^2$ to about $1.20 \times 10^{-3}$ inches$^2$.

42. The catheter of claim 33 wherein the cross-sectional area of the first portion of the third lumen is from about $3.48 \times 10^{-3}$ inches$^2$ to about $3.15 \times 10^{-3}$ inches$^2$ and the cross-sectional area of the second portion of the third lumen is from about $1.42 \times 10^{-4}$ inches$^2$ to about $1.07 \times 10^{-3}$ inches$^2$.

43. The catheter of claim 42, wherein the main body has an external wall and interluminal walls wherein the external and interluminal walls have a minimum thickness of about .006 inches, and wherein the distal end has an external wall and interluminal walls wherein the external and interluminal walls have a minimum thickness of about .004 inches.

44. The catheter of claim 33 wherein the first shape is a kidney shape and the second shape is a crescent shape.

45. The catheter of claim 33 or 42 wherein the main body has an external wall and interluminal walls wherein the external and interluminal walls have a minimum thickness of about .006 inches.

46. The catheter of claim 33 or 42 wherein the distal end has an external wall and interluminal walls wherein the external and interluminal walls have a minimum thickness of about .004 inches.

* * * * *

UNITED STATES PATENT AND TRADEMARK OFFICE
CERTIFICATE OF CORRECTION

PATENT NO. : 7,481,800 B2
APPLICATION NO. : 10/182346
DATED : January 27, 2009
INVENTOR(S) : Steven L. Jacques It is certified that error appears in the above-identified patent and that said Letters Patent is hereby corrected as shown below:

Column 2, line 5 please delete "deflation times where" and replace with --deflation times were--.

Column 9, line 49 claim 5 please delete "$2.07 \times 10^{-4}$ inches$^2$." and replace with --$2.07 \times 10^{-4}$" inches$^2$.--.

Column 9, line 53 claim 6 please delete "$9.14 \times 10^{-5}$ inches$^2$." and replace with --$9.14 \times 10^{-5}$ inches$^2$.--.

Column 10, line 12 claim 13 please delete "third lumen" and replace with --the third lumen--.

Column 10, line 36 claim 14 please delete "$2.07 \times 10^{-4}$ inches" and replace with --$2.07 \times 10^{-4}$ inches$^2$--.

Column 10, line 43 claim 15 please delete "$1.19 \times 10^{-3}$ inches" and replace with --$1.19 \times 10^{-3}$ inches$^2$--.

Column 12, line 41 claim 29 please delete "$1.20 \times 10^{-3}$ inches" and replace with --$1.20 \times 10^{-3}$ inches$^2$.--.

Column 13, line 25 claim 38 please delete "$\times 10^{-5}$ inches" and replace with --$\times 10^{-5}$ inches$^2$--.

UNITED STATES PATENT AND TRADEMARK OFFICE
CERTIFICATE OF CORRECTION

PATENT NO. : 7,481,800 B2
APPLICATION NO. : 10/182346
DATED : January 27, 2009
INVENTOR(S) : Steven L. Jacques It is certified that error appears in the above-identified patent and that said Letters Patent is hereby corrected as shown below:

Column 14, line 9 claim 42 please delete "$x10^{-3}$ inches$^2$" and replace with --$x10^{-4}$ inches$^2$--.

Signed and Sealed this

Twenty-sixth Day of May, 2009

JOHN DOLL
*Acting Director of the United States Patent and Trademark Office*